United States Patent

Sicheneder et al.

Patent Number: 5,276,206
Date of Patent: Jan. 4, 1994

[54] METHOD OF PREPARING 2-MERCAPTOBENZOTHIAZOLE AND BENZOTHIAZOLE

[75] Inventors: Adolf Sicheneder; Bardo Becker, both of Dormagen, Fed. Rep. of Germany

[73] Assignee: Bayer Aktiengesellschaft, Leverkusen, Fed. Rep. of Germany

[21] Appl. No.: 61,229

[22] Filed: May 17, 1993

[30] Foreign Application Priority Data

May 27, 1992 [DE] Fed. Rep. of Germany ....... 4217541

[51] Int. Cl.$^5$ ............................................. C07D 209/02
[52] U.S. Cl. ..................................... 548/152; 548/175
[58] Field of Search ................................. 548/152, 175

[56] References Cited

U.S. PATENT DOCUMENTS 4,429,134  1/1984  Papenfuhs ............................ 548/152

OTHER PUBLICATIONS

CA 116:108044v Differential ... polyisoprene, Luyt, p. 87, 1992.

Primary Examiner—Mary C. Lee
Assistant Examiner—Joseph K. McKane
Attorney, Agent, or Firm—Connolly & Hutz

[57] ABSTRACT 2-mercaptobenzothiazole and benzothiazole are prepared from dibenzothiazyl disulphide by reacting dibenzothiazyl disulphide in the presence of an alkali and/or alkaline earth hydroxide solution at temperatures from 40° to 120° C. until a constant pH value in the range from 8 to 10 has been reached, then treating the reaction mixture with an aqueous solution of mineral acids at temperatures from 10° to 100° C., and subsequently removing benzothiazole by distillation or extraction from the reaction mixture containing 2-mercaptobenzothiazole.

1 Claim, No Drawings

METHOD OF PREPARING 2-MERCAPTOBENZOTHIAZOLE AND BENZOTHIAZOLE

This invention relates to a method of preparing 2-mercaptobenzothiazole (MBT) and benzothiazole (BT) from dibenzothiazyl disulphide (MBTS) by treating the reaction mixture first with an aqueous alkaline solution and then with an aqueous solution of mineral acids.

The preparation of 2-mercaptobenzothiazole and the preparation of benzothiazole by the reaction of aniline with $CS_2$ and sulphur is known (see U.S. Pat. No. 1,631,871). Depending on the process conditions, a mixture of MBT/BT can be obtained, wherein the composition is about 10:1. Since only small amounts of benzothiazole result from this method of preparation, in addition to a larger amount of mercaptobenzothiazole, the availability of the desired benzothiazole from this method is limited.

The preparation of 2-mercaptobenzothiazole in addition to benzothiazole can also be effected by the photolysis of dibenzothiazyl disulphide, sulphur also being produced in addition, however (see Z. Naturforsch., B: Chem. Sci. 1987, 42(9), 1153 to 1158). This method is unsuitable for the large-scale industrial manufacture of MBT and BT.

A method has now been found for the preparation of 2-mercaptobenzothiazole and benzothiazole from dibenzothiazyl disulphide, which is characterized in that dibenzothiazyl disulphide is reacted in the presence of an alkali- and/or alkaline earth hydroxide solution at temperatures from 40° to 120° C. until a constant pH value in the range from 8 to 10 has been reached, the reaction mixture is then treated with an aqueous solution of mineral acids at temperatures from 10° to 100° C., and the benzothiazole is subsequently removed by distillation or extraction from the reaction mixture containing 2-mercaptobenzothiazole.

The 2-mercaptobenzothiazole is obtained from the reaction mixture by filtration.

Treatment of the dibenzothiazyl disulphide with an alkali- and/or alkaline earth hydroxide solution is preferably carried out at temperatures from 80° to 100° C.

The concentration of the alkali- and/or alkaline earth hydroxide solutions used is generally 10 to 50 weight %, preferably 20 to 30 weight %. LiOH, NaOH, KOH and $Ca(OH)_2$ may be used as the alkali and alkaline earth hydroxides, with NaOH being preferred.

In the method according to the invention, 0.9 to 1.2 moles, preferably 1.0 to 1.1 moles, of alkali- and/or alkaline earth hydroxide are used.

Treatment of the dibenzothiazyl disulphide with an alkali- and/or alkaline earth hydroxide solution is continued until a constant pH value has been reached. At the end of this treatment the pH value is about 8 to 10 (fluctuation: ±0.05 units).

After the pH value has become constant, the reaction mixture is treated with an aqueous solution of mineral acids, preferably at temperatures from 20° to 80° C. Hydrochloric, sulphuric, nitric and/or phosphoric acids may be used as the mineral acids. Sulphuric acid is preferred. The aqueous solutions of the mineral acids (10 to 50%) are added in amounts of about 0.7 to 1.3, preferably 0.9 to acid equivalents, with respect to the base equivalents used. It is also possible to introduce acid gases such as HCl or $SO_2$ directly into the aqueous reaction mixture.

During the treatment of the reaction mixture with the aqueous mineral acid solution the composition of the product mixture can be regulated by appropriately controlling the temperature. Higher temperatures (>40° C.) favour the formation of 2-mercaptobenzothiazole. At lower temperatures (10° to 40° C.) the formation of benzothiazole is enhanced.

A good yield of product is obtained from the method according to the invention if the benzothiazole formed is continuously removed from the reaction mixture. This can be achieved, for example, by steam distillation (generally at atmospheric pressure) or by extraction with an organic solvent which is immiscible with water, such as cyclohexane, hexane, benzene, toluene, xylene, methyl tert.-butyl ether and/or tert.-amyl methyl ether.

Furthermore, in the method according to the invention it is possible to influence the yield of benzothiazole and mercaptobenzothiazole by varying the amount of base or acid. With equimolar amounts or a deficit (about 10 mole %) of base, an MBT:BT ratio of 3:1 is obtained. With an excess of base (about 15 weight %), the molar amount of 2-mercaptobenzothiazole obtained is five times that of benzothiazole in the ideal case.

The method according to the invention is suitable for the large-scale industrial manufacture of 2-mercaptobenzothiazole and benzothiazole. The compound used as the starting material in the method, dibenzothiazyl disulphide, is an easily accessible intermediate product which is used in the manufacture of vulcanisation agents. Dibenzothiazyl disulphide is easily accessible from several routes; thus, for example, 2-mercaptobenzothiazole can be reacted with oxygen to form the disulphide, using a suitable catalyst system. Chorine has hitherto been used industrially as the oxidizing agent. In the preparation of 2-mercaptobenzothiazole and benzothiazole from dibenzothiazyl disulphide according to the invention, it is surprising that the hydrolysis (disproportionation) of dibenzothiazyl disulphide in alkaline media does not lead to cleavage of the thiazole system and that the subsequent desulphonation proceeds smoothly under the given conditions. Furthermore, it is surprising that the MBT/BT ratio can be reproducibly adjusted in the range from 5:1 to 3:1 by variation of the reaction parameters. The reaction system thus permits the reaction to be carried out in a defined manner according to need with regard to the amounts of products required.

EXAMPLES

Example 1

150 parts by weight $H_2O$ and
23.2 parts by weight of NaOH
were introduced into a 500 ml four-necked flask fitted with a plastic-coated glass stirrer, thermometer, dropping funnel and reflux condenser and heated to 50° C.
85.4 parts by weight of dibenzothiazyl disulphide (MBTS; 98%)
were then added and the mixture heated to 90° C. After 1 hour,
160 parts by weight of an $H_2SO_4$ solution (20%)
were added drop-wise over about 30 minutes. The benzothiazole (BT) azeotrope formed was then distilled off. A suspension of 2-mercaptobenzothiazole (MBT) in dilute sulphuric acid remained in the flask. After cooling, the solid was filtered off and washed until it was neutral. After drying, a product was obtained comprising 69.5 parts by weight MBT (96%) and
11.7 parts by weight BT (98%).

The MBT/BT molar ratio was 4.7:1.

Example 2

150 parts by weight H₂O and
20.2 parts by weight of NaOH
were introduced into a 500 ml four-necked flask fitted with a plastic-coated stirrer, thermometer, dropping funnel and reflux condenser and heated to 50° C.
85.4 parts by weight of MBTS (98%)
were then added and the mixture heated to 90° C. After 1 hour,
160 parts by weight of an H₂SO₄ solution (20%)
were added drop-wise over about 30 minutes. The benzothiazole azeotrope formed was then distilled off. After cooling, the remaining MBT suspension was filtered off and the filter cake was washed until it was neutral and then dried. A product was obtained comprising
66.1 parts by weight MBT (96%) and
14.4 parts by Weight BT (98%).

The MBT/BT molar ratio was 3.6:1.

Example 3

Hydrolysis in an alkaline medium was effected as in Example 1. After a reaction time of 1 hour a constant pH value had been reached, and sufficient 20% sulphuric acid was added at 80° C. to adjust the pH to 2. The benzothiazole azeotrope formed was then distilled off. The remaining suspension was worked up as in the previous examples to give a product comprising
66.1 parts by weight MBT (95%) and
10.9 parts by weight BT (99%).

The MBT/BT molar ratio was 4.8:1.

Example 4

200 parts by weight H₂O
20.6 parts by weight NaOH, and
85.4 parts by weight MBTS (98%)
were introduced into the apparatus described in Example 1 and the suspension was heated to 90° C. The resulting solution was stirred for one hour at this temperature and sulphuric acid was then added drop-wise at about 80° C. to give a pH of 4. About 90 g of a 20% H₂SO₄ solution was used.
100 parts by weight of cyclohexane
were then added to this suspension, and the mixture was refluxed for 15 minutes. It was then cooled, and the solid was filtered off and washed with water until neutral.

The organic phase of the filtrate was separated off and the solvent distilled off.

A product was obtained comprising
65.6 parts by weight MBT (content: 98.5%), and
11.4 parts by weight BT (content: 91.6%).

The MBT/BT molar ratio was 5:1.

We claim:

1. A method of preparing 2-mercaptobenzothiazole and benzothiazole from dibenzothiazyl disulphide, characterized in that dibenzothiazyl disulphide is reacted in the presence of an alkali- and/or alkaline earth hydroxide solution at temperatures from 40° to 120° C. until a constant pH value in the range from 8 to 10 has been reached, the reaction mixture is then treated with an aqueous solution of mineral acids at temperatures from 10° to 100° C., and benzothiazole is subsequently removed by distillation or extraction from the reaction mixture containing 2-mercaptobenzothiazole.

* * * * *